(12) United States Patent
Pazicky et al.

(10) Patent No.: US 10,941,092 B2
(45) Date of Patent: Mar. 9, 2021

(54) HYDROFORMYLATION PROCESS FOR PRODUCING 1,6-HEXANEDIOL DERIVATIVES

(71) Applicant: BASF SE, Ludwigshafen am Rhein (DE)

(72) Inventors: Marek Pazicky, Ludwigshafen am Rhein (DE); Martin Ernst, Ludwigshafen am Rhein (DE); Nicolas Marion, Saint-Louis (FR); Rocco Paciello, Ludwigshafen am Rhein (DE); Johann-Peter Melder, Ludwigshafen am Rhein (DE); Hermann Luyken, Ludwigshafen am Rhein (DE)

(73) Assignee: BASF SE

( * ) Notice: Subject to any disclaimer, the term of this patent is extended or adjusted under 35 U.S.C. 154(b) by 0 days.

(21) Appl. No.: 16/621,050

(22) PCT Filed: Jun. 6, 2018

(86) PCT No.: PCT/EP2018/064844
§ 371 (c)(1),
(2) Date: Dec. 10, 2019

(87) PCT Pub. No.: WO2018/228879
PCT Pub. Date: Dec. 20, 2018

(65) Prior Publication Data
US 2020/0172458 A1 Jun. 4, 2020

(30) Foreign Application Priority Data

Jun. 13, 2017 (EP) .................................. 17175673

(51) Int. Cl.
C07C 29/141 (2006.01)
C07D 317/26 (2006.01)
B01J 31/18 (2006.01)
C07C 31/20 (2006.01)

(52) U.S. Cl.
CPC .......... C07C 29/141 (2013.01); B01J 31/186 (2013.01); C07D 317/26 (2013.01); B01J 2231/321 (2013.01); B01J 2531/822 (2013.01); C07C 31/20 (2013.01)

(58) Field of Classification Search
CPC .... C07C 29/141; C07D 317/26; B01J 31/186; B01J 2231/321; B01J 2531/822; B01J 31/0202; B01J 2231/643; B01J 31/0237; B01J 2540/10; B01J 31/185; B01J 31/04
See application file for complete search history.

(56) References Cited

U.S. PATENT DOCUMENTS

| | | | |
|---|---|---|---|
| 3,947,503 A | 3/1976 | Kummer | |
| 5,312,996 A | 5/1994 | Packett | |
| 6,642,420 B1 | 11/2003 | Zehner et al. | |
| 6,881,867 B2 | 4/2005 | Ahlers et al. | |
| 6,977,312 B2 | 12/2005 | Ahlers et al. | |
| 7,015,361 B2 | 3/2006 | Zehner et al. | |
| 7,145,042 B2 | 12/2006 | Volland et al. | |
| 7,173,138 B2 | 2/2007 | Ahlers et al. | |
| 8,110,709 B2 | 2/2012 | Papp et al. | |
| 10,315,975 B2 | 6/2019 | Strautmann et al. | |
| 2004/0110960 A1 | 6/2004 | Ahlers et al. | |

FOREIGN PATENT DOCUMENTS

| | | |
|---|---|---|
| DE | 10052462 A1 | 5/2002 |
| EP | 423769 A2 | 4/1991 |
| EP | 1114017 A1 | 7/2001 |
| EP | 1223155 A1 | 7/2002 |
| EP | 1231198 A1 | 8/2002 |
| GB | 1581379 A | 12/1980 |
| WO | WO-0009467 A1 | 2/2000 |
| WO | WO-0158589 A1 | 8/2001 |
| WO | WO-0222261 A2 | 3/2002 |
| WO | WO-02083695 A1 | 10/2002 |
| WO | WO-2003018192 A2 | 3/2003 |
| WO | 10342760 A1 | 3/2004 |

(Continued)

OTHER PUBLICATIONS

International Search Report for PCT/EP2018/064844 dated Jul. 17, 2018.

(Continued)

*Primary Examiner* — Rosalynd A Keys

(74) *Attorney, Agent, or Firm* — Faegre Drinker Biddle & Reath LLP

(57) ABSTRACT

The present invention relates to a two-stage hydroformylation process for producing pound of the formula (I) and to a process for producing a compound of the formula (V) comprising the two-stage hydroformylation process for producing a compound of the formula (I) followed by hydrogenation of the compound of the formula (I).

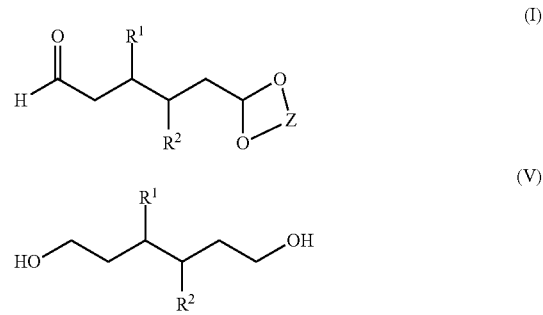

11 Claims, No Drawings

(56) References Cited

FOREIGN PATENT DOCUMENTS

| WO | WO-2004026803 A1 | 4/2004 |
| WO | WO-2005009934 A2 | 2/2005 |
| WO | WO-2005039762 A1 | 5/2005 |
| WO | WO-2005063730 A1 | 7/2005 |
| WO | WO-2017064064 A1 | 4/2017 |

OTHER PUBLICATIONS

Written Opinion of the International Searching Authority for PCT/EP2018/064844 dated Jul. 17, 2018.
European Search Report for EP Patent Application No. 17175673.7, dated Aug. 10, 2017, 4 pages.
Lu, et al., "An Efficient Method for the Acetalization of $\alpha,\beta$-Unsaturated Aldehydes", The Journal of Organic Chemistry, vol. 60, Issue 9, May 1, 1995, pp. 2931-2934.
Mormul, et al., "Supporting Information :Synthesis of Adipic Acid, 1,6-Hexanediamine, and 1,6-Hexanediol via Double-n-Selective Hydroformylation of 1,3-Butadiene 3 Isomerizing hydroformylation within situ acetalization", ACS Catalysis, vol. 6, Issue 5, Jun. 5, 2016, pp. 1-18.
Mormul, et al., "Synthesis of Adipic Acid, 1,6-Hexanediamine, and 1,6-Hexanediol via Double-n-Selective Hydroformylation of 1,3-Butadiene", ACS Catalysis, vol. 6, Issue 5, Mar. 2016, pp. 2802-2810.

HYDROFORMYLATION PROCESS FOR PRODUCING 1,6-HEXANEDIOL DERIVATIVES

CROSS-REFERENCE TO RELATED APPLICATIONS

This application is a national stage application (under 35 U.S.C. § 371) of PCT/EP2018/064844, filed Jun. 6, 2018, which claims benefit of European Application No. 17175673.7, filed Jun. 13, 2017, both of which are incorporated herein by reference in their entirety.

DESCRIPTION

The present invention relates to a two-stage hydroformylation process for producing a compound of the formula (I)

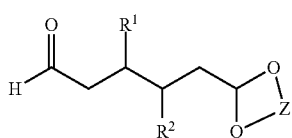

(I)

and to a process for producing a compound of the formula (V)

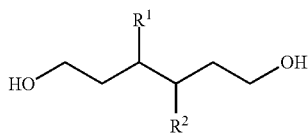

(V)

comprising the two-stage hydroformylation process for producing a compound of the formula (I) followed by hydrogenation of the compound of the formula (I).

1,6-Hexanediol derivatives, in particular 1,6-hexanediol itself, are produced on a large scale in the chemical industry. These compounds are of commercial interest in particular for the production of polymers like polyesters and polyurethanes.

1,6-Hexanediol is largely produced via hydrogenation of adipic acid, while adipic acid is produced in the industry mainly via oxidation of cyclohexanol with nitric acid. This process of the prior art is disadvantageous because nitrogen oxides are formed during the process from the nitric acid which have to be destroyed or employed in other processes. Furthermore, cyclohexanol is an expensive compound. The hydroxycarboxylation of butadiene with carbon monoxide and water to obtain adipic acid is known in the prior art. However, this process was never employed on a larger scale in the industry because it suffers from low selectivity for adipic acid and problems concerning its isolation.

In order to overcome the disadvantages of the processes for the production of 1,6-hexanediol, different approaches have been suggested in the prior art.

U.S. Pat. No. 3,947,503 discloses a multi-step process for the production of 1,6-hexanediol from butadiene. In the first step, butadiene is subjected to a reaction with carbon monoxide and hydrogen in the presence of a rhodium complex and an alkanol or alkanediol to obtain the mono-acetal of 3-pentenal (penten-3-al-dimethylacetal). In the second step, the mono-acetal of 3-pentenal is reacted with carbon monoxide and hydrogen in the presence of a cobalt complex to a mixture of valeraldehyde-acetal, formylvaleraldehyde-acetal and hydroxymethylvaleraldehyde-acetal. In the third step, the resulting mixture is subjected to a hydrogenation reaction in the presence of a hydrogenation catalyst. This process is disadvantageous for following reasons. The yield of 1,6-hexanediol based on the starting material butadiene is low. In this process, a high amount of undesirable by-products is formed. The regioselectivity for 1,6-hexanediol is not satisfactory (82% first hydroformalytion to penten-3-al-acetal and 89% second hydroformylation to 1,6-Hexandiol).

U.S. Pat. No. 5,312,996 discloses a process for the production of 1,6-hexanedial by the reaction of butadiene with carbon monoxide and hydrogen under catalytic reaction of rhodium complexes. Also reactions in the presence of diols are described. The yield of 1,6-hexanedial based on the starting material butadiene is low. A high amount of undesirable by-products is formed, in particular unsaturated and saturated mono-acetals and branched diacetals. The regioselectivity for 1,6-hexanedial is not satisfactory (Example 1 with 61% valeraldehyde, 1% pentenals, 11% branched dialdehyde and 25% adipaldehyde).

EP1223155 describes a process for the preparation of a caprolactam precursor starting from butadiene, whereby the process comprises a step in which butadiene is hydroformylated in the presence of an alcohol resulting in a reaction mixture comprising an acetal of pentenals, which are subsequently converted to methyl-3-pentenoate by oxidation. (Example I with 39% linear 3- and 4-penenal and 4% linear pentanal. The second step, example VI with 20% conversion with 12% selectivity to dimethylacetal of 5-formylvalerate using dimethylacetal of 3-pentenal).

ACS Catal. 2016, 6, 2802-2810 discloses an investigation on the synthesis of adipic acid, 1,6-hexadiamine, and 1,6-hexandiol via a double-n-selective hydroformylation of 1,3-butadiene. The key intermediate is adipic aldehyde diacetal. The described concentrations of the starting material butadiene in the experiments is very low and not sufficient in view of a technical and economical practical process.

GB 1 581 379 discloses the preparation of diols by hydrogenation and hydrolysis of aldehydes comprising in addition a cyclic acetal as second functional group.

The processes of the prior art are connected with disadvantages. The 1,6-difunctionalized hexane derivatives are obtained in low regioselectivities and low yields or in an insufficient spacetime yield in the processes of the prior art. In known hydroformylations of 1,3-di-unsaturated compounds, in particular butadiene, the regioselectivity for the 1,6-isomer of the dialdehyde over the undesirable 1,2-, 1,3- and 1,4-isomers of the dialdehyde is generally not satisfactory. The processes of the prior art yield a number of by-products. In the hydroformylation of butadiene, these are particularly mono-unsaturated pentenals, pentanal and the undesirable regioisomers 1,2-hexanedial, 1,3-hexanedial and 1,4-hexanedial.

Proceeding from this prior art, it is an object of the invention to provide a technical and economic process for the production of 1,6-hexanediol derivatives and their corresponding precursors, which comprise in the 1 and 6 position of the precursor an aldehyde group or an acetal group.

This object is achieved by a two-stage hydroformylation process for producing a compound of the formula (I)

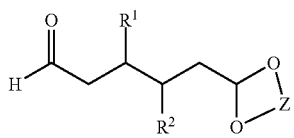 (I)

wherein
$R^1$ and $R^2$ are independently from each other hydrogen or linear or branched $C_1$-$C_4$-alkyl,
Z is a hydrocarbon chain having 2 or 3 carbon atoms which is unsubstituted or substituted and which may be part of a carbocycle, a heterocycle or an aromatic or heteroaromatic ring,
comprising the process steps:
a) reacting at least one compound of the formula (II)

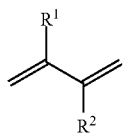 (II)

wherein $R^1$ and $R^2$ have the same meaning as in formula (I),
with carbon monoxide and hydrogen in the presence of at least one transition metal catalyst TMC 1,
wherein the reaction is performed in the presence of at least one alkanol of the formula (III)

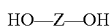
HO—Z—OH (III)

wherein Z has the same meaning as in formula (I),
and in the presence of at least one acid,
to obtain a reaction mixture comprising at least one compound selected from the compounds of the formulas (IVa), (IVb'), (IVb"), (IVc') and (IVc"),

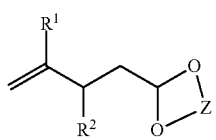 (IVa)

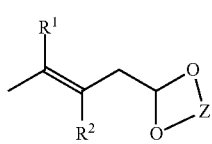 (IVb')

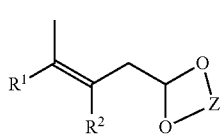 (IVb")

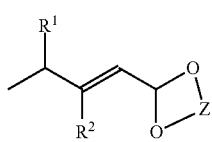 (IVc')

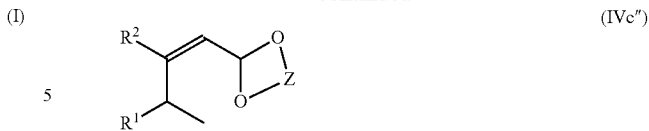 (IVc")

wherein $R^1$, $R^2$ and Z have the same meaning as in formula (I),
b) separation of the reaction mixture formed in process step a) to obtain a fraction enriched with at least one compound selected from the compounds of the formulas (IVa), (IVb'), (IVb"), (IVc') and (IVc") and depleted from the alkanol of the formula (III) and from the transition metal catalyst TMC 1,
c) reacting the fraction enriched with at least one compound selected from the compounds of the formulas (IVa), (IVb'), (IVb"), (IVc') and (IVc") obtained in process step b) with carbon monoxide and hydrogen in the presence of at least one transition metal catalyst TMC 2 and at least one organic base to obtain the compound of the formula (I),
wherein the organic base is used in a molar amount, which is equivalent or higher than the molar amount of the acid, which was used in process step a), and which is present in the fraction obtained in process step b), and
d) optionally separation of the reaction mixture formed in process step c) to obtain a fraction enriched with the compound of the formula (I).

A further aspect of the present invention provides a process for producing a compound of the formula (V)

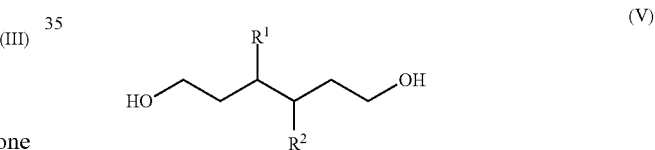 (V)

wherein
$R^1$ and $R^2$ are independently from each other hydrogen or linear or branched $C_1$-$C_4$-alkyl,
comprising the process steps a), b), c) and d) for producing a compound of the formula (I) as described above,

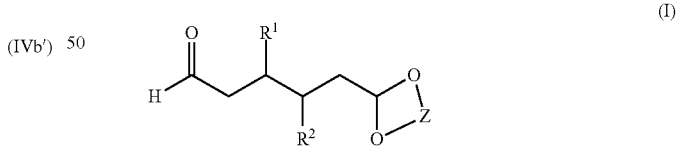 (I)

wherein
$R^1$ and $R^2$ have the same meaning as in formula (V) and
Z is a hydrocarbon chain having 2 or 3 carbon atoms which is unsubstituted or substituted and which may be part of a carbocycle, a heterocycle or an aromatic or heteroaromatic ring,
followed by a process step:
i) reacting the compound of formula (I) with hydrogen in the presence of at least one transition metal catalyst TMC 3 and in the presence of water, preferably wherein the molar ratio of water to the compound of formula (I) is at least 1, wherein during the hydrogenation in process step i) the temperature is increased for at least 20 K from a temperature $T_1$ to a temperature $T_2$.

In process step a) of the two above-described processes of the invention, at least one compound of the formula (II) is subjected to a reaction, more precisely to a hydroformylation reaction, with carbon monoxide and hydrogen in the presence of at least one transition metal catalyst TM1, at least one alkanol of the formula (III) and at least one acid.

The at least one compound of the formula (II) which is employed in step a) of the processes of the invention is a 1,3-diunsaturated hydrocarbon which is unsubstituted or substituted with linear or branched $C_1$-$C_4$-alkyl in the 2- and 3-position. Preferably, the at least one compound of the formula (II) is selected from butadiene, isoprene and 2,3-dimethylbutadiene. Most preferred is butadiene.

In one embodiment of the present invention, the process is characterized in that the at least one compound of the formula (II) is butadiene.

The initial concentration of the at least one compound of the formula (II) in process step a) can be varied in a wide range. Preferably, the initial concentration of the at least one compound of the formula (II) in the process step a) is in the range from 10 to 50 wt.-%, more preferably in the range from 15 to 40 wt.-% by weight based on the total weight of all components of the reaction mixture.

In one embodiment of the present invention, the process is characterized in that the initial concentration of the at least one compound of the formula (II) in the process step a) is in the range from 10 to 50 wt.-%, preferably in the range from 15 to 40 wt.-% by weight based on the total weight of all components of the reaction mixture.

The at least one alkanol of the formula (III) which is present in step i) of the process of the invention is an at least diol which is able to form stable acetals with the aldehyde groups formed in the compounds of the formula (II) under the conditions of the hydroformylation reaction. The at least one alkanol of the formula (III) is an at least diol in which two hydroxyl groups are linked over a hydrocarbon chain having 2 or 3 carbon atoms which is unsubstituted or substituted and which may be part of a carbocycle, a heterocycle or an aromatic or heteroaromatic ring. Suitable alkanols of the formula (III) are selected from 1,2-ethanediol, 1,2-propanediol, 1,3-propanediol, 2-methyl-1,3-propanediol, 2,2-dimethyl-1,3-propanediol, 1,2,3-propanediol (glycerol), diglycerol (a mixture of glycerol dimers coupled at primary and secondary hydroxyl groups), 2,2-dimethyl-1,3-propanediol, 3-mercaptopropane-1,2-diol (thioglycerol), dithiothreitol, 1,1,1-trimethylolpropane, 1,2-butanediol, 1,3-butanediol, 2,4-butanediol, 2,4-dimethyl-2,4-butanediol, pentaerythritol, cyclohexane-1,2-diol, 1,4-dioxane-2,3-diol, 1,2,3-butanetriol, 1,3,4-butanetriol, 1,2,3-heptanetriol, 4-menthane-1,7,8-triol, 3-butene-1,2-diol, benzene-1,2-diol (catechol), 3-chlorocatechol, indane-1,2-diol, tartaric acid and pentose and hexose sugars including mannitol, sorbitol, xylitol, threitol, erythritol, maltitol and lactitol. Particularly preferred alkanols of the formula (III) are 1,2-ethanediol, 1,2-propanediol, 1,3-propanediol, 2-methyl-1,3-propanediol, 2,2-dimethyl-1,3-propanediol, 2,4-butanediol, 2,4-dimethyl-2,4-butanediol and benzene-1,2-diol (catechol). Most preferred is 1,2-ethanediol.

In one embodiment of the present invention, the process is characterized in that the at least one alkanol of the formula (III) is 1,2-ethanediol (ethylene glycol).

Preferably, the at least one alkanol of the formula (III) is employed in excess compared to the at least one compound of the formula (II), preferably butadiene. The molar ratio of the at least one compound of the formula (II) to the at least one alkanol of the formula (III) is preferably in the range from 1:1 to 1:100.

In one embodiment of the present invention, the process is characterized in that the molar ratio of the at least one compound of the formula (II) to the at least one alkanol of the formula (III) is in the range from 1:1 to 1:100.

Process step a) of the invention is performed in the presence of at least one acid. In principle, all acids can be employed which catalyze the formation of acetals from aldehydes and alkanols. The acid catalyzes the acetal formation of the first hydroformylation product with the at least one alkanol of the formula (III) in order to obtain a compound selected from the compounds of the compounds of the formulas (IVa), (IVb'), (IVb"), (IVc') and (IVc"). Principally suitable acids are Bronsted acids, Lewis acids and mixtures thereof. Particularly preferred are Bronsted acids.

The $pK_a$-value relative to water of the at least one acid can be varied in a wide range. Preferably the acid used in process step a) has a $pK_a$-value relative to water in the range from −14 to 7, preferably in the range from −3 to 6, more preferably in the range from −2 to 5.

Preferred examples of suitable acids are trifluoroacetic acid, formic acid, hydrochloric acid, sulfuric acid, nitric acid, acidic pyridinium salts and p-toluenesulfonic acid. Also preferred are acidic ion exchangers, in particular sulfonated polystyrenes. Particularly preferred is trifluoroacetic acid.

In one embodiment of the present invention, the process is characterized in that the acid used in process step a) has a $pK_a$-value relative to water in the range from −14 to 7, preferably in the range from −3 to 6, more preferably in the range from −2 to 5.

In process step b) of the two above-described processes of the invention, the reaction mixture obtained in step a) is subjected to a separation to obtain a fraction enriched with at least one compound selected from the compounds of the formulas (IVa), (IVb'), (IVb"), (IVc') and (IVc") and depleted from the alkanol of the formula (III) and from the transition metal catalyst TMC 1. In process step b) at least one further fraction is obtained enriched with the alkanol of the formula (III) and with the transition metal catalyst TMC 1. Preferably, at least 50 wt.-%, more preferably at least 75 wt.-% and particularly preferably at least 90 wt.-% of the compounds of the formulas (IVa), (IVb'), (IVb"), (IVc') and (IVc"), based on the total weight of the compounds of the formula of the formulas (IVa), (IVb'), (IVb"), (IVc') and (IVc") in the reaction mixture, are separated from the reaction mixture obtained in step a).

In the separation step b), the compounds of the formulas (IVa), (IVb'), (IVb"), (IVc') and (IVc") are preferably separated from non-converted compounds of the formula (II) and (III), the transition metal catalyst TCM 1, by-products and, if present, the solvent.

The separation of the compounds of the formulas (IVa), (IVb'), (IVb"), (IVc') and (IVc") in step b) can principally be performed by all separation methods known to a person skilled in the art. Preferably, the compounds of the formulas (IVa), (IVb'), (IVb"), (IVc') and (IVc") are separated by distillation, crystallization, extraction, adsorption or a combination of these methods. Particularly preferably, the compounds of the formulas (IVa), (IVb'), (IVb"), (IVc') and (IVc") are separated by distillation. The distillation in step b) can be performed by methods which are principally known to a person skilled in the art. Preferably, the distillation is performed in a vaporizer or in a distillation unit comprising a vaporizer and one or more distillation columns with trays or a packing.

The at least one further fraction, which is obtained in process step b) and which is enriched with non-converted compounds of the formula (II), in particular butadiene, with the alkanol of the formula (III) and with the transition metal catalyst TMC 1, can be at least partially recycled to process step a). The transition metal catalyst TMC 1 can generally be employed for further hydroformylations in process step a). It is particularly preferred to recycle the least one further fraction to step a) in the preferred embodiments in which the process is performed continuously or semicontinuously.

In process step c) of the two above-described processes of the invention, the fraction, which is enriched with at least one compound selected from the compounds of the formulas (IVa), (IVb'), (IVb"), (IVc') and (IVc") and which was obtained in process step b), is subjected to a reaction, more precisely to a second hydroformylation reaction, with carbon monoxide and hydrogen in the presence of at least one transition metal catalyst TMC 2 and in the presence of at least one organic base in order to obtain the compound of the formula (I).

In process step a) and c) of the two above-described processes of the invention, at least one transition metal catalyst is employed. In principle, all transition metal catalysts which are known to catalyze hydroformylation reactions can be employed in the process of the invention. Such catalysts are described, for example, in WO 01/58589, WO 02/083695, WO 02/22261, WO 03/018192, WO 2004/026803, WO 2005/009934, WO 2005/039762, WO 2005/063730, DE 103 42 760 A1 and DE 100 52 462 A1, in particular in DE 100 52 462 A1 and WO 02/083695.

The at least one transition metal catalyst, in process step a) named TMC 1 and in process c) named TMC 2, comprises at least one transition metal and at least one ligand, preferably a phosphorous-containing ligand, in particular a phosphorous-containing bidentate ligand.

The at least one transition metal catalyst, TMC 1 or TMC 2, preferably comprises at least one transition metal selected from the transition metals of the groups 8, 9 and 10 of the periodic table of the elements according to IUPAC. Preferably, the at least one transition metal is selected from Co, Ru, Ir, Rh, Ni, Pd, Pt and mixtures thereof. More preferably, the at least one transition metal is Rh.

In one embodiment of the present invention, the process is characterized in that the at least one transition metal catalyst TMC 1 used in process step a) comprises at least one transition metal selected from Co, Ru, Ir, Rh, Ni, Pd and Pt, preferably Rh.

In another embodiment of the present invention, the process is characterized in that the at least one transition metal catalyst TMC 2 used in process step c) comprises at least one transition metal selected from Co, Ru, Ir, Rh, Ni, Pd and Pt, preferably Rh.

Transition metal catalysts TMC 1 and TCM 2 can be different or they can be identical.

In one embodiment of the present invention, the process is characterized in that the at least one transition metal catalyst TMC 1 used in process step a) and the at least one transition metal catalyst TMC 2 used in process step c) both comprise Rh.

The at least one transition metal catalyst, TMC 1 or TMC 2, preferably comprises at least one ligand which comprises at least one atom selected from P, As and Sb. More preferably, the at least one ligand comprises at least one P atom.

In one embodiment of the present invention, the process is characterized in that the at least one transition metal catalyst TMC 1 used in process step a) and the at least one transition metal catalyst TMC 2 used in process step c) each comprise independently from each other at least one phosphine ligand which is bound over P atoms to a transition metal.

In the sense of the invention, the expression "alkyl" means straight and branched alkyl groups. Preferred are straight or branched $C_1$-$C_{20}$-alkyl groups, more preferably $C_1$-$C_{12}$-alkyl groups, even more preferably $C_1$-$C_8$-alkyl groups and in particular $C_1$-$C_6$-alkyl groups. Examples of alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethyl butyl, 1,3-di methyl butyl, 2,3-di methyl butyl, 1,1-di methyl butyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

The expression "alkyl" comprises also substituted alkyl groups, which may carry 1, 2, 3, 4 or 5 substituents, preferably 1, 2 or 3 substituents and particularly preferably 1 substituent, selected from the groups cycloalkyl, aryl, hetaryl, halogen, $NE^1E^2$, $NE^1E^2E^{3+}$, COOH, carboxylate, $SO_3H$ and sulfonate. A preferred fluorinated alkyl group is trifluoromethyl. The expression "alkyl" also comprises alkyl groups which are interrupted by one or more non-adjacent oxygen atoms, preferably alkoxyalkyl.

The expression "alkylene" in the sense of the present invention stands for straight or branched alkanediyl groups with preferably 1 to 6 carbon atoms. These are methylene (—$CH_2$—), ethylene (—$CH_2$—$CH_2$—), n-propylene (—$CH_2$—$CH_2$—$CH_2$—), isopropylene (—$CH_2$—$CH$($CH_3$)—), etc.

The expression "cycloalkyl" in the sense of the present invention comprises unsubstituted and substituted cycloalkyl groups, preferably $C_5$-$C_7$-cycloalkyl groups like cyclopentyl, cyclohexyl or cycloheptyl, which in case they are substituted may carry 1, 2, 3, 4 or 5 substituents, preferably 1, 2 or 3 substituents and particularly preferred 1 substituent selected from the groups alkyl, alkoxy and halogen.

The expression "heterocycloalkyl" in the sense of the present invention comprises saturated or partially unsaturated cycloaliphatic groups with preferably 4 to 7, more preferably 5 or 6 ring atoms, in which 1, 2, 3 or 4 ring atoms may be substituted with heteroatoms, preferably selected from the elements oxygen, nitrogen and sulfur and which are optionally substituted. In case they are substituted, these heterocycloaliphatic groups carry preferably 1, 2 or 3 substituents, more preferably 1 or 2 substituents and in particular 1 substituent. These substituents are preferably selected from alkyl, cycloalkyl, aryl, COOR (R=H, alkyl, cycloalkyl, aryl), COO$^-$M$^+$ and $NE^1E^2$, more preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

The expression "aryl" in the sense of the present invention comprises unsubstituted and substituted aryl groups and preferably stands for phenyl, tolyl, xylyl, mesityl, naphthyl, fluorenyl, anthracenyl, phenanthrenyl or naphthacenyl, more preferably phenyl or naphthyl. In case these aryl groups are substituted they may carry preferably 1, 2, 3, 4 or 5 substituents, more preferably 1,2 oder 3 substituents and particulary preferred 1 substituent. These substituents are preferably selected from the groups alkyl, alkoxy, carboxyl, carboxylate, trifluoromethyl, —SO$_3$H, sulfonate, NE$^1$E$^2$, alkylene-NE$^1$E$^2$, nitro, cyano and halogen. A preferred fluorinated aryl group is pentafluorophenyl.

The expression "hetaryl" in the sense of the present invention comprises unsubstituted or substituted heterocycloaromatic groups, preferably pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl in which in case these heterocycloaromatic groups are substituted they may carry preferably 1, 2 or 3 substituents selected from the groups alkyl, alkoxy, carboxyl, carboxylate, —SO$_3$H, sulfonate, NE$^1$E$^2$, alkylene-NE$^1$E$^2$, trifluoromethyl and halogen. A preferred substituted indolyl group is 3-methyl-indolyl.

Carboxylate and sulfonate in the sense of the present invention preferably stand for a derivative of a carboxylic acid function or a sulfonic acid function, in particular a metal carboxylate or metal sulfonate, a carboxylic acid ester or sulfonic acid ester or a carboxylic acid amide or sulfonic acid amide. Particularly preferred are esters with C$_1$-C$_4$-alkanols like methanol, ethanol, n-propanol, isopropanol, n-butanol, sec-butanol and tert-butanol. Preferred are also the primary amides and their N-alkyl and N,N-dialkyl derivatives.

The above statements regarding the expressions "alkyl", "cycloalkyl", "aryl", "heterocycloalkyl" and "hetaryl" apply accordingly to the expressions "alkoxy", "cycloalkoxy", "aryloxy", "heterocycloalkoxy" and "hetaryloxy".

The expression "acyl" in the sense of the present invention stands for alkanoyl groups or aroyl groups with preferably 2 to 11, more preferably 2 to 8 carbon atoms, for example acetyl, propanoyl, butanoyl, pentanoyl, hexanoyl, heptanoyl, 2-ethylhexanoyl, 2-propylheptanoyl, benzoyl and naphthoyl.

The groups NE$^1$E$^2$ and NE$^4$E$^5$ are preferably selected from N,N-dimethylamino, N,N-diethylamino, N,N-dipropylamino, N,N-diisopropylamino, N,N-di-n-butylamino, N,N-di-tert-butylamino, N,N-dicyclohexylamino and N,N-diphenylamino.

Halogen stands for fluorine, chlorine, bromine or iodine, preferably fluorine, chlorine or bromine.

M$^+$ stands for a cation equivalent, which means a monovalent cation or the part of a polyvalent cation representing a positive single charge. The cation M$^+$ is only a counter ion which neutralizes negatively charged substituents like the COO$^-$ or the sulfonate group and which can principally be selected arbitrarily. Preferred are alkaline metal ions, in particular Na$^+$, K$^+$ and Li$^+$ ions, or onium ions like ammonium ions, mono-, di-, tri-, tetraalkylammonium ions, phosphonium ions, tetraalkylphosphonium ions and tetraarylphosphonium ions.

The same applies to the anion equivalent X$^-$ which is only a counter ion for positively charged substituents like the ammonium group and which can principally be selected arbitrarily among monovalent anions and the parts of polyvalent anions which correspond to a single negative charge. Preferred are halogenides X$^-$, in particular chloride and bromide. Also preferred are sulfates and sulfonates, in particular SO$_4^{2-}$, tosylate, trifluoromethane sulfonate and methylsulfonate.

Condensed ring systems are aromatic, heteroaromatic or cyclic compounds which have fused-on rings obtained via anellation. Condensed ring systems consist of two, three or more than three rings. Depending on the type of connection, one distinguishes between ortho-anellation and peri-anellation. In case of ortho-anellation each ring has two atoms in common with each adjacent ring. In case of peri-anellation a carbon atoms belongs to more than two rings. Preferred among the condensed ring systems are ortho-condensed ring systems.

In a preferred embodiment of the invention, the at least one transition metal catalyst comprises at least one ligand of the formula (VI)

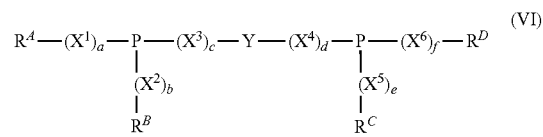

wherein

R$^A$, R$^B$, R$^C$ and R$^D$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, SO$_3$H, sulfonate, NE$^1$E$^2$, NE$^1$E$^2$E$^{3+}$X$^-$, halogen, nitro, formyl, acyl and cyano, wherein E$^1$, E$^2$ and E$^3$ are the same or different and are selected from hydrogen, alkyl, cycloalkyl, and aryl and X$^-$ is an anion equivalent, and wherein the radicals cycloalkyl, heterocycloalkyl, aryl and hetaryl R$^A$, R$^B$, R$^C$ and R$^D$ may carry 1, 2, 3, 4 or 5 substituents selected from alkyl and the substituents mentioned for the alkyl radicals R$^A$, R$^B$, R$^C$ and R$^D$ before, or R$^A$ and R$^B$ and/or R$^C$ and R$^D$ together with the P atom and, if present, the groups X$^1$, X$^2$, X$^5$ and X$^6$ to which they are bound, are a 5- to 8-membered heterocycle, which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, SO$_3$H, sulfonate, NE$^4$E$^5$, NE$^4$E$^5$E$^{6+}$X$^-$, nitro, alkoxycarbonyl, formyl, acyl and cyano, wherein E$^4$, E$^5$ and E$^6$ are the same or different and are selected from hydrogen, alkyl, cycloalkyl and aryl and X$^-$is an anion equivalent, X$^1$, X$^2$, X$^3$, X$^4$, X$^5$ and X$^6$ are independently from each other O, S, SiR$^x$R$^y$ or NR$^z$, wherein R$^x$, R$^y$ and R$^z$ are independently from each other hydrogen, alkyl, cycloalkyl, heterocycloalkyl, aryl or hetaryl, Y is a divalent bridging group which contains carbon atoms, and a, b, c, d, e and f are independently from each other 0 or 1.

In another preferred embodiment of the invention, the at least one transition metal catalyst comprises at least one ligand of the formula (VI.1)

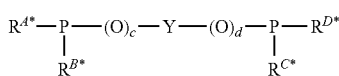
(VI.1)

wherein

Y is a divalent bridging group which contains carbon atoms, c and d are independently from each other 0 or 1, and the radicals $R^{A*}$, $R^{B*}$, $R^{C*}$ and $R^{D*}$ are independently from each other selected from the groups of the formula (VIII.a) to (VIII.k)

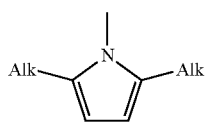
(VIII.a)

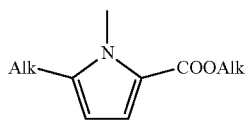
(VIII.b)

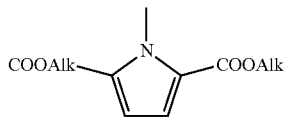
(VIII.c)

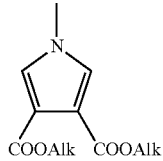
(VIII.d)

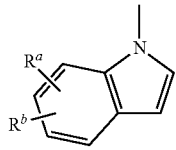
(VIII.e)

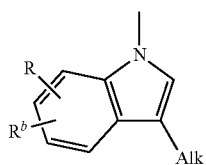
(VIII.f)

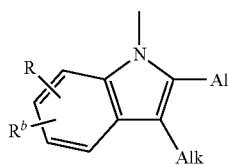
(VIII.g)

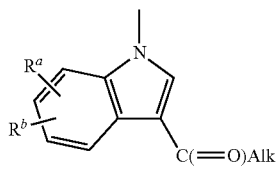
(VIII.h)

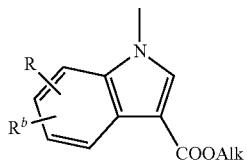
(VIII.i)

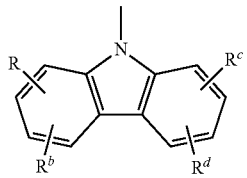
(VIII.k)

wherein

Alk is a $C_1$-$C_4$-alkyl group, and $R^a$, $R^b$, $R^c$ and Rd are independently from each other hydrogen, $C_1$-$C_4$-alkyl, $C_1$-$C_4$-alkoxy, formyl, acyl, halogen, $C_1$-$C_4$-alkoxycarbonyl or carboxyl. Particularly preferred groups $R^a$, $R^b$, $R^c$ and $R^d$ are methyl, ethyl, n-propyl, isopropyl, n-butyl, tert-butyl and trifluoromethyl.

In another preferred embodiment of the invention, the at least one transition metal catalyst comprises at least one ligand of the formula (IX)

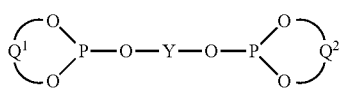
(IX)

wherein

Y is a divalent bridging group which contains carbon atoms, $Q^1$ and $Q^2$ are independently from each other a divalent bridging group of the formula (X),

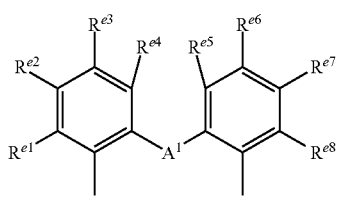
(X)

wherein $R^{e1}$, $R^{e2}$, $R^{e3}$, $R^{e4}$, $R^{e5}$, $R^{e6}$, $R^{e7}$ and $R^{e8}$ are independently from each other hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy, halogen, hydroxy, mercapto, cyano, nitro, formyl, acyl, carboxy, carboxylate, alkylcarbonyloxy, carbamoyl, $SO_3H$, sulfonate or $NE^1E^2$, wherein $E^1$ and $E^2$ are the same or different and are selected from hydrogen, alkyl, cycloalkyl, heterocycloalkyl, aryl and hetaryl, wherein two adjacent radicals $R^{e1}$ to $R^{e8}$ together with the carbon atoms of the benzene ring to which they are bound may also be a condensed ring system with 1, 2 or 3 further rings, and $A^1$ is a single bond, O, S, $NR^{a31}$, $SiR^{a32}R^{a33}$ or $C_1$-$C_4$-alkylene, which may have a double bond and/or which may be substituted with alkyl, cycloalkyl, heterocycloalkyl, aryl or hetaryl or which may be interrupted by O, S, $NR^{a31}$ or $SiR^{a32}R^{a33}$, wherein $R^{a31}$, $R^{a32}$ and $R^{a33}$ are independently from each other hydrogen, alkyl, cycloalkyl, heterocycloalkyl, aryl or hetaryl.

The divalent bridging group Y is a divalent bridging group which contains carbon atoms. The divalent bridging group Y is preferably selected from the groups of the formula (XI.a) to (XI.u)

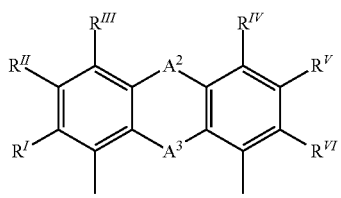
(XI.a)

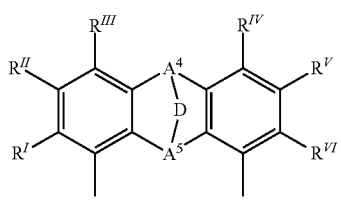
(XI.b)

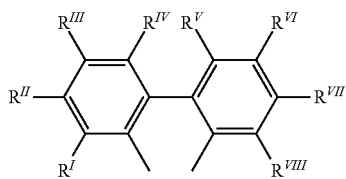
(XI.c)

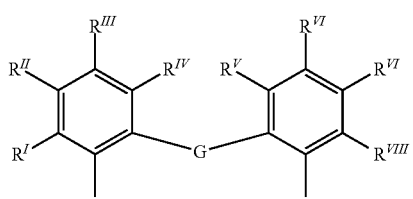
(XI.d)

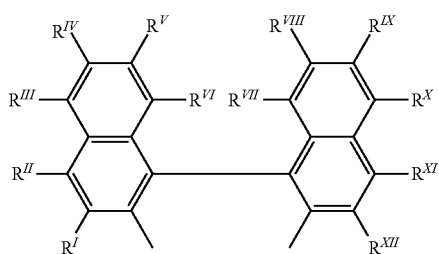
(XI.e)

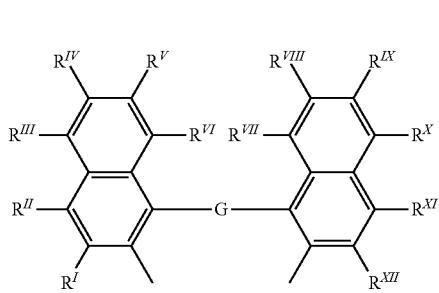
(XI.f)

-continued

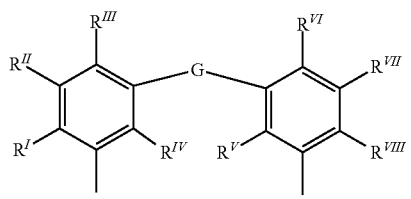
(XI.g)

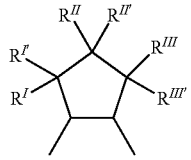
(XI.h)

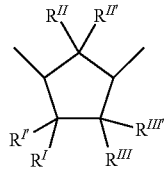
(XI.i)

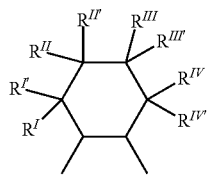
(XI.k)

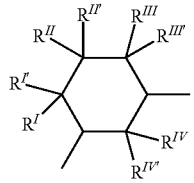
(XI.l)

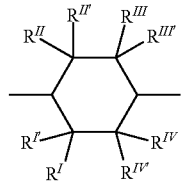
(XI.m)

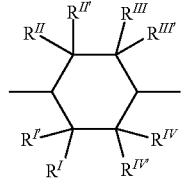
(XI.n)

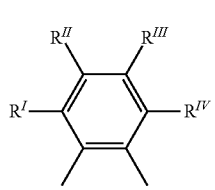
(XI.o)

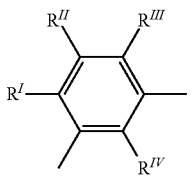 (XI.p)

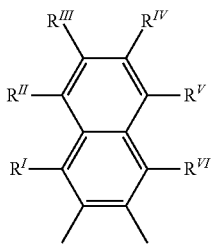 (XI.q)

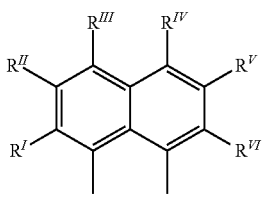 (XI.r)

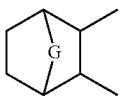 (XI.s)

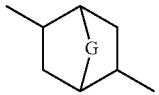 (XI.t)

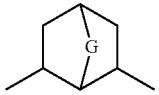 (XI.u)

wherein $R^I, R^{I'}, R^{II}, R^{II'}, R^{III}, R^{III'}, R^{IV}, R^{IV'}, R^V, R^{VI}, R^{VII}, R^{VIII}, R^{IX}, R^X, R^{XI}$ and $R^{XII}$ are each, independently from each other, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, wherein $E^1$ and $E^2$ are identical or different and are selected from hydrogen, alkyl, cycloalkyl and aryl, G is O, S, $NR^\delta$ or $SiR^\delta R^\epsilon$, wherein $R^\delta$ and $R^\epsilon$ are each, independently from each other, hydrogen, alkyl, cycloalkyl, heterocycloalkyl, aryl or hetaryl, or G is a $C_1$-$C_4$-alkylene bridge which may have a double bond and/or which carries an alkyl, cycloalkyl, heterocycloalkyl, aryl or hetaryl substituent, or G is a $C_2$-$C_4$-alkylene bridge which is interrupted by O, S or $NR^\delta$ or $SiR^\delta R^\epsilon$, wherein in the groups of the formula (XI.a) and (XI.b), two adjacent radicals $R^I$ to $R^{VI}$ together with the carbon atoms of the benzene ring to which they are bound may also form a fused ring system having 1, 2 or 3 further rings, wherein in the groups of the formula (XI.h) to (XI.n), two geminal radicals $R^I, R^{I'}; R^{II}, R^{II'}; R^{III}, R^{III'}$ and/or $R^{IV}, R^{IV'}$ may also represent oxo or a ketal thereof, $A^2$ and $A^3$ are each, independently from each other, O, S, $SiR^\Phi R^\gamma$, $NR^\eta$ or $CR^L R^\kappa$, wherein $R^\Phi, R^\gamma, R^\eta, R^L$ and $R^\kappa$ are each, independently from each other, hydrogen, alkyl, cycloalkyl, heterocycloalkyl, aryl or hetaryl, $A^4$ and $A^5$ are each, independently from each other, $SiR^\Phi$, N or $CR^L$, D is a divalent bridging group of the formula

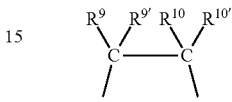

wherein $R^9, R^{9'}, R^{10}$ and $R^{10'}$ are each, independently from each other, hydrogen, alkyl, cycloalkyl, aryl, halogen, trifluoromethyl, carboxyl, carboxylate or cyano, wherein $R^{9'}$ together with $R^{10'}$ may also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, wherein the heterocycle and, if present, the fused-on groups may each carry, independently from each other, 1, 2, 3 or 4 substituents selected from alkyl, cycloalkyl, heterocycloalkyl, aryl, hetaryl, $COOR^f$, $COO^-M^+$, $SO_3R^f$, $SO_3^-M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, wherein $R^f, E^4, E^5$ and $E^6$ are the same or different and are selected from hydrogen, alkyl, cycloalkyl and aryl, $R^e$ is hydrogen, methyl or ethyl, $M^+$ is a cation equivalent, $X^-$ is an anion equivalent, and y is an integer from 1 to 240.

Particularly preferred are divalent bridging groups Y of the formula (XI.b) and (XI.c).

In the preferred divalent bridging groups Y of the formula (XI.b), a particularly preferred divalent bridging group D is the ethylene group —$CH_2$—$CH_2$—. Accordingly, the divalent bridging groups Y of the formula (XI.b) have preferably a triptycene-like carbon skeleton.

In the preferred divalent bridging groups Y of the formula (XI.c), the substituents $R^I$ to $R^{VIII}$ are preferably selected from hydrogen, alkyl and alkoxy.

In one embodiment of the present invention, the process is characterized in that the at least one transition metal catalyst TMC 1 used in process step a) and the at least one transition metal catalyst TMC 2 used in process step c) both comprise at least one bidentate ligand selected from the compounds of the formula (VI.a), (VI.b), (VI.c), (VI.d) and (VI.e), preferably (VI.c).

(VI.a)

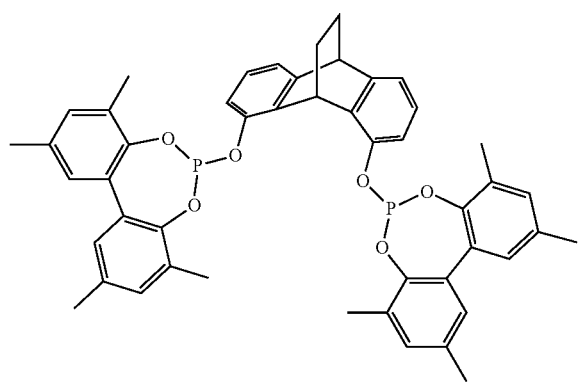

(VI.b)

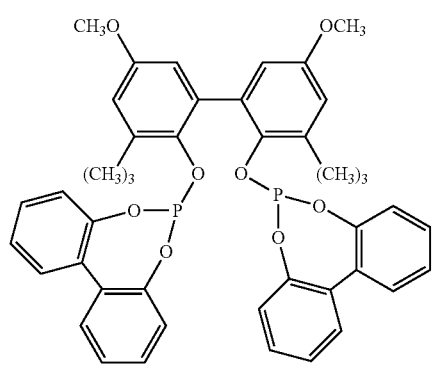

(VI.c)

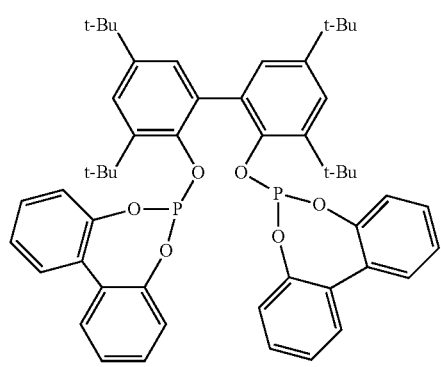

(VI.d)

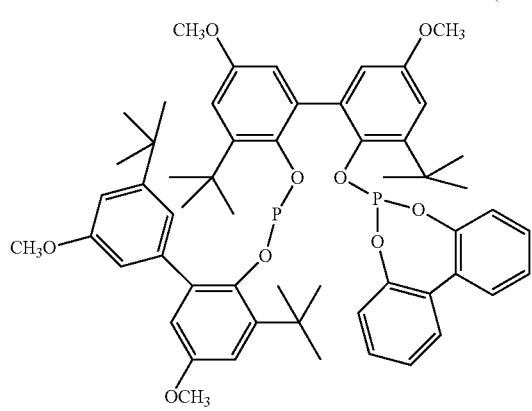

(VI.e)

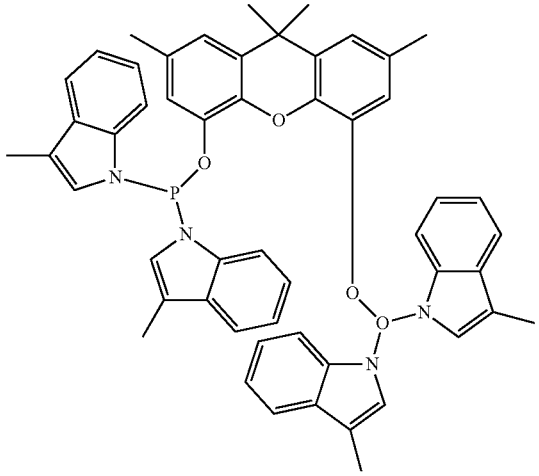

In addition to the ligands described before, the at least one transition metal catalyst, TMC 1 or TMC 2, can have at least one further ligand which is preferably selected from halogenides, amines, carboxylates, acetylacetonate, arylsulfonates or alkylsulfonates, hydride, CO, olefins, dienes, cycloolefines, nitriles, N-containing heterocycles, aromates and heteroaromates, ethers, $PF_3$, phosphols, phosphabenzenes and monodentate ligands selected from phosphines, phosphinites, phosphonites, phosphoramidites and phosphites. Additional ligands which are particularly preferred are hydride, carbonyl and triphenylphosphine. The at least one transition metal catalyst, TMC 1 or TMC 2, can contain more than one additional ligand which can also be different ligands. Particularly preferably the at least one transition metal catalyst, TMC 1 or TMC 2, contains hydride and carbonyl. In particular the at least one transition metal catalyst, TMC 1 or TMC 2, contains one ligand of the formula (VI), (VI.1) or (IX) and hydride or one ligand of the formula (VI), (VI.1) or (IX) and carbonyl.

The amount of the transition metal in the at least one transition metal catalyst, preferably Rh, is preferably in the range from 0.1 to 5000 ppm based on the weight of the at least one transition metal catalyst, TMC 1 or TMC 2.

The molar ratio of the preferred phosphorous-containing ligands, preferably a ligand of the formula (VI), (VI.1) or (IX), to the at least one transition metal is preferably in the range from 1:1 to 1000:1, more preferably in the range from 1:1 to 500:1.

The transition metal catalysts TMC 1 and TMC 2, which are in principle soluble transition metal catalysts, can be produced beforehand and employed in their active form in the process of invention. The transition metal catalysts can also be produced from transition metal sources under addition of the ligands, preferably the ligands of the formula (VI), (VI.1) or (IX), under the reaction conditions of the hydroformylation. In a preferred embodiment, the at least one transition metal catalyst is produced in the reaction mixture of the hydroformylation wherein at least one of the ligands of the formula (VI), (VI.1) or (IX), a compound or a complex of the transition metal and optionally an activating agent are reacted in an inert solvent under the hydroformylation conditions.

Suitable transition metal sources are principally transition metals, transition metal compounds and transition metal complexes from which the transition metal catalyst is formed under the hydroformylation conditions.

Suitable as a transition metal sources are particularly rhodium compounds or rhodium complexes. Preferred rhodium compounds or rhodium complexes are rhodium(II) salts and rhodium(III) salts like rhodium(II) carboxylate and rhodium(III) carboxylate, rhodium(II) acetate and rhodium (III) acetate, etc. Further suitable are rhodium complexes like rhodiumbiscarbonylacetylacetonate, acetylacetonatobisethylenerhodium(I) acetylacetonatocyclooctadienylrhodium(I), acetylacetonatonorbornadienylrhodium(I), acetylacetonatocarbonyltriphenylphosphinerhodium(I), etc. Particularly preferred transition metal sources are selected from rhodiumbiscarbonylacetylacetonate, rhodium(II) acetate and rhodium(III) acetate.

The temperature and the pressure during the hydroformylation reactions in process step a) and c) of the two above-described processes of the invention can be varied independently in a wide range. Preferably the temperature during process step a) is lower than the temperature during process step c) and the pressure during process step a) is higher than the pressure during process step c). Preferably the difference between the temperature during process step a) and the temperature during process step c) is at least 10 K, more preferably 20 K, in particular 30 K.

Preferably the difference between the pressure during process step a) and the pressure during process step c) is at least 2 bar, more preferably 5 bar, in particular 10 bar.

The temperature during process step a) is preferably at least 20° C., more preferably the temperature during process step a) is in the range from 30 to 90° C., in particular in the range from 50 to 70° C. The temperature during process step c) is preferably at least 60° C., more preferably the temperature during process step c) is in the range from 70 to 130° C., in particular in the range from 90 to 110° C.

In one embodiment of the present invention, the process is characterized in that the temperature during process step a) is in the range from 30 to 90° C., more preferably in the range from 50 to 70° C., the temperature during process step c) is in the range from 70 to 130° C., more preferably in the range from 90 to 110° C. and the difference between the temperature during process step a) and the temperature during process step c) is at least 20 K, more preferably at least 30 K.

In the hydroformylation reactions in process step a) and in process step c), a gas mixture of carbon monoxide and hydrogen is employed. The molar ratio of carbon monoxide to hydrogen can principally be varied over a broad range. The molar ratio of carbon monoxide to hydrogen is generally in the range from 5:1 to 1:5, preferably in the range from 60:40 to 40:60. Particularly preferably, a gas mixture of carbon monoxide and hydrogen is employed in process step a) and in process step c), wherein the molar ratio of carbon monoxide to hydrogen is about 1:1.

The hydroformylation reactions in process step a) and in process step c) are generally performed at the partial pressure of the gas mixture of carbon monoxide and hydrogen at the respective reaction temperature. Preferably, the pressure of the gas mixture of carbon monoxide and hydrogen is in the range from 1 to 300 bar, more preferably from 1 to 100 bar and even more preferably from 1 to 50 bar.

The pressure during process step a) is preferably at least 10 bar, more preferably the pressure during process step a) is in the range from 20 to 70 bar, in particular in the range from 25 to 50 bar. The pressure during process step c) is preferably at least 1 bar, more preferably the pressure during process step c) is in the range from 2 to 15 bar, in particular in the range from 3 to 7 bar.

In one embodiment of the present invention, the process is characterized in that the pressure during process step a) is in the range from 20 to 70 bar, the pressure during process step c) is in the range from 2 to 15 bar and the difference between the pressure during process step a) and the pressure during process step c) is at least 5 bar.

In one embodiment of the present invention, the process is characterized in that the hydroformylation reaction in process step a) is performed at a temperature in the range from 30 to 90° C., more preferably in the range from 50 to 70° C. and at a pressure in the range from 20 to 70 bar, in particular in the range from 25 to 50 bar, the hydroformylation reaction in process step c) is performed at a temperature in the range from 70 to 130° C., more preferably in the range from 90 to 110° C. and at a pressure the range from 2 to 15 bar, in particular in the range from 3 to 7 bar and the molar ratio of carbon monoxide to hydrogen is preferably about 1:1.

The temperature and the pressure during the hydroformylation reactions in process step a) and c) of the two above-described processes of the invention can be varied independently in a wide range. Preferably the temperature during process step a) is lower than the temperature during process step c) and the pressure during process step a) is higher than the pressure during process step c). Preferably the difference between the temperature during process step a) and the temperature during process step c) is at least 10 K, more preferably 20 K, in particular 30 K. Preferably the difference between the pressure during process step a) and the pressure during process step c) is at least 2 bar, more preferably 5 bar, in particular 10 bar.

The period of times, in which the hydroformylation reactions in process step a) and c) of the two above-described processes of the invention are performed, can be varied in wide range, depending in particular on the chosen reaction temperature, the pressure of carbon monoxide and hydrogen, the concentration of the olefinic compound and and the concentration of the transition metal catalyst.

Process step a) is preferably performed for a period of time in the range from 0.1 to 48 h, preferable from 0.5 to 24 h, in particular form 1 to 12 h. Process step c) is preferably performed for a period of time in the range from 0.01 to 24 h, preferable from 0.1 to 12 h, in particular form 1 to 6 h.

At least 20° C., more preferably the temperature during process step a) is in the range from 30 to 90° C., in particular in the range from 50 to 70° C. The temperature during process step c) is preferably at least 60° C., more preferably the temperature during process step c) is in the range from 70 to 130° C., in particular in the range from 90 to 110° C.

The hydroformylation reactions in process step a) and in process step c) are generally performed in a reaction zone which may comprise one or more reactors which may be the same or different. In the simplest case, the reaction zone is formed by a single reactor. The reactors may have the same or different mixing characteristics. The reactors may be divided into two or more different sections by built-in components. In case the reaction zone is formed by two or more reactors, the reactors may be connected in any possible order, for example in parallel or in series. Suitable reactors are principally all reactors which can be employed for hydroformylation reactions, for example stirred reactors, bubble column reactors, for example those described in U.S. Pat. No. 4,778,929, circulation reactors, for example those described in EP-A 1 114 017, tube reactors, wherein the respective reactors may have different mixing characteristics as described in EP-A 423 769. Further suitable reactors are compartmented reactors as described in EP-A 1 231 198 or U.S. Pat. No. 5,728,893. Suitable reactors are principally known to a person skilled in the art and are described in known reference work related to industrial chemistry such as "Ullmanns Enzyklopädie der technischen Chemie". Suitable pressure-resistant reactors are also known to a person skilled in the art. Preferably, for the process of the invention an autoclave is employed which may have an internal stirrer and an internal lining.

A person skilled in the art knows, in principle, how to perform a reaction with a gas mixture in which the defined temperature and a defined pressure is chosen and will select the reactors and the combination of the reactors accordingly.

The hydroformylation reactions of process step a) and of process step c) can principally be performed continuously, semicontinuously or discontinuously.

The hydroformylation reactions of process step a) and of process step c) can be performed in a solvent which is inert under the reaction conditions. Suitable solvents are preferably aromates like toluene and xylenes, hydrocarbons and mixtures of hydrocarbons, esters of aliphatic carboxylic acids with alkanols, for example Texanol®, esters of aromatic carboxylic acids, for example $C_8$-$C_{13}$-dialkylphthalates and ethers, for example tert-butylmethyl ether or tetrahydrofurane. In case the preferred compounds of the formula (VI), (VI.1) or (IX) are sufficiently hydrophilic, also ketones like acetone or methylethylketone are preferred as solvents. In principle, also ionic liquids can be employed as solvents. Preferred ionic liquids are N,N'-dialkylimidazolium salts, for example N-butyl-N'-methylimidazolium salts, tetraalkylammonium salts, for example tetra-n-butylammonium salts, N-alkylpyridinium salts, for example N-butylpyridinium salts, tetraalkylphosphonium salts, for example trishexyl(tetradecyl)phosphonium salts, in particular the tetrafluoroborates, acetates, tetrachloroaluminates, hexafluorophosphates, chlorides and tosylates of these salts. In principle, also water or water-containing solvents can be employed as solvents in the hydroformylation. Preferred water-containing solvents are mixtures of water with ketones, preferably acetone or methylethylketone.

The separation of the compound of the formula (IV) in process step b) can principally be performed by all separation methods known to a person skilled in the art. Preferably, the compound of the formula (I) is separated by distillation, crystallization, extraction, adsorption or a combination of these methods. Particularly preferably, the compound of the formula (IV) is separated by distillation. The distillation in step d) can be performed by methods which are principally known to a person skilled in the art. Preferably, the distillation is performed in a vaporizer or in a distillation unit comprising a vaporizer and one or more distillation columns with trays or a packing.

The at least one further fraction, which is obtained in process step b) and which is enriched with the transition metal catalyst TMC 1 can be at least partially recycled to process step a). The transition metal catalyst TMC 1 can generally be employed for further hydroformylations in process step a). It is particularly preferred to recycle the least one further fraction to step a) in the preferred embodiments in which the process is performed continuously or semicontinuously.

The yield of the compounds of the formula (I) in reaction step c) is generally at least 50%, preferably at least 70% and particularly preferably at least 85%, based on the amount of the at least one compound of the formula (II) employed reaction step a).

The regioselectivity in reaction step c) for the 1,6-disubstituted compounds of the formula (I) over the 1,2-, 1,3- and 1,4-disubstituted compounds is generally at least 55%, preferably at least 70% and particularly preferably at least 85%, based on the reacted amounts of the at least one compound of the formula (II) in reaction step a).

In process step c) the organic base is used in a molar amount, which is equivalent or higher than the molar amount of the acid, which was used in process step a), and which might be still present in the fraction obtained in process step b). The organic base is used in an amount which is at least sufficient for complete neutralization of any residual acid, which might be present in the fraction, which is enriched with at least one compound selected from the compounds of the formulas (IVa), (IVb'), (IVb''), (IVc') and (IVc'') and which was obtained in process step b). The reaction mixture of process step c) is neutral or basic, so that any acetal cleavage and acetal formation is extremely slow or does not take place at all.

Preferably the organic base is a nitrogen containing compound such as an amine, preferably an alkyl substituted amine, or an amidine, preferably an alkyl substituted amidine.

Non limiting examples of suitable organic bases ethyl amine, di-isopropyl-amine, tri-ethyl-amine, tri-dodecyl-amine, quinuclidine, morpholine, DABCO or DBU.

In one embodiment of the present invention, the process is characterized in that the organic base used in process step c) is an amine of formula (VII)

(VII)

wherein
$R^3$ is hydrogen or an organic radical selected from linear or branched, substituted or unsubstituted $C_1$-$C_{30}$-alkyl,
$R^4$ and $R^5$ are independently from each other hydrogen or an organic radical selected from linear or branched, substituted or unsubstituted $C_1$-$C_{30}$-alkyl,
or two adjacent radicals of the group of radicals consisting of $R^3$, $R^4$ and $R^5$ together with the atoms connecting them form a monocyclic or polycyclic, substituted or unsubstituted, aliphatic ring system which has from 4 to 40 carbon atoms and can also com-prise heteroatoms selected from the group consisting of the elements N, P, O and S.

In a further embodiment of the present invention, the process is characterized in that the molar ratio of the organic base to the at least one transition metal catalyst TMC 2 used in process step c) is in the range from 0.5 to 20, preferably in the range from 1 to 10, more preferably in the range from 1.5 to 5, in particular in the range from 2 to 3. Protonated organic base, that is for example an alkyl ammonium cation, the reaction product of an alkyl amine with the proton of an acid, is not considered as an organic base in the above-mentioned molar ratio of the organic base to the at least one transition metal catalyst TMC 2 used in process step c).

In optional process step d) of the two above-described processes of the invention, the reaction mixture formed in process step c) is subjected to a separation to obtain a fraction enriched with the compound of the formula (I) and depleted from the transition metal catalyst TMC 2, the organic base, any used solvents and any side products. In process step d) at least one further fraction is obtained enriched with the transition metal catalyst TMC 2. Preferably, at least 70 wt.-%, more preferably at least 80 wt.-% and particularly preferably at least 90 wt.-% of the compound of the formula (I), based on the total weight of the compounds of the formula of the formula (I) in the reaction mixture, are separated from the reaction mixture obtained in step c).

In the separation step d), the compound of the formula (I) is preferably separated from the transition metal catalyst TCM 2, by-products and, if present, the solvent.

The separation of the compound of the formula (I) in step d) can principally be performed by all separation methods known to a person skilled in the art. Preferably, the compound of the formula (I) is separated by distillation, crystallization, extraction, adsorption or a combination of these methods. Particularly preferably, the compound of the formula (I) is separated by distillation. The distillation in step d) can be performed by methods which are principally known to a person skilled in the art. Preferably, the distillation is performed in a vaporizer or in a distillation unit comprising a vaporizer and one or more distillation columns with trays or a packing.

The at least one further fraction, which is obtained in process step d) and which is enriched with the transition metal catalyst TMC 2 can be at least partially recycled to process step c). The transition metal catalyst TMC 2 can generally be employed for further hydroformylations in process step c). It is particularly preferred to recycle the least one further fraction to step c) in the preferred embodiments in which the process is performed continuously or semicontinuously.

In process step i) of the above-described process of the invention, the compound of formula (I), which is obtained in process steps c) or d), is reacted with hydrogen in the presence of at least one transition metal catalyst TMC 3 and in the presence of water, wherein during the hydrogenation in process step i) the temperature is increased for at least 20 K from a temperature $T_1$ to a temperature $T_2$ in order to obtain the compound of the formula (V).

While the free aldehyde functional group of the compound of formula (I) can be directly hydrogenated at a temperature $T_1$, the acetal group of the compound of formula (I) predominantly reacts with water at a temperature $T_2$ in order to generate a second aldehyde functional group, which is subsequently hydrogenated at the temperature $T_2$.

Temperatures $T_1$ and $T_2$ can be varied in a wide range, depending on the activity of the hydrogenation catalyst and on the desired reaction rate of the acetal cleavage with water. Preferably $T_1$ is in the range from 0 to 200° C., more preferably from 40 to 120° C. and $T_2$ is in the range from 100 to 300° C., more preferably from 140 to 220° C.

In one embodiment of the present invention, the process is characterized in that in process step i) $T_1$ is in the range from 40 to 120° C. and $T_2$ is in the range from 140 to 220° C.

The hydrogenation can principally be performed according to all processes known to a person skilled in the art which are suitable for the hydrogenation of aldehydes to alkanols.

Preferably, the hydrogenation in process step i) is performed in the presence of at least one transition metal catalyst TMC 3, which is a hydrogenation catalyst. In principle, all catalysts can be employed which are known to a person skilled in the art for the hydrogenation of aldehydes to alkanols. The transition metal catalyst TMC 3 can be homogeneous or heterogeneous. Particularly preferred transition metal catalysts TMC 3 are those which are stable in the presence of water. Preferred transition metal catalyst TMC 3 comprises at least one transition metal selected from Ru, Ir, Rh, Ni, Pd and Pt, preferably Ni.

In one embodiment of the present invention, the process is characterized in the that at least one transition metal catalyst TMC 3 used in process step i) comprises at least one transition metal selected from Ru, Ir, Rh, Ni, Pd and Pt, preferably Ni.

Process step i) is performed in the presence of water, which is necessary for the conversion of the acetal group of the compound on the formula (I) into an aldehyde group. In principle, the molar ratio of water to the compound of formula (I) can be varied in a wide range, e.g. in the range of 0.1 to 1000, preferably 0.8 to 100, more preferably 1 to 60, in particular 10 to 30. To convert all acetal groups into aldehyde groups one equivalent water per acetal group is necessary. Higher amounts of water in a reaction mixture shift the equilibrium between acetal and aldehyde to the aldehyde. Further solvents may be present during the hydrogenation. Preferred are those solvents which are mentioned above as preferred for the hydroformylation of reaction step a) or c).

In one embodiment of the present invention, the process is characterized in that in reaction step i) the molar ratio of water to the compound of formula (I) is in the range from 1 to 60, more preferably from 10 to 30.

Since the formation of an acetal group and the cleavage of an acetal group is catalyzed by protons, the hydrogenation of the compound on the formula (I) is preferably performed in the presence of a proton generating compound, also called an acid.

Preferably, the hydrogenation in process step i) is performed in the presence of at least one acid. Principally suitable acids are Bronsted acids, Lewis acids and mixtures thereof. Particularly preferred are Bronsted acids. Preferred examples of suitable acids are trifluoroacetic acid, formic acid, hydrochloric acid, sulfuric acid, nitric acid, acidic pyridinium salts and p-toluenesulfonic acid. Also preferred are acidic ion exchangers, in particular sulfonated polystyrenes. In a preferred embodiment, the acid is an acidic material which is insoluble in the reaction mixture, preferably an acidic support material of a heterogeneous hydrogenation catalyst.

The hydrogenation in reaction step i) may be performed continuously, semicontinuously or discontinuously.

The hydrogenation reaction in in reaction step i) can principally be performed in all reactors known by a person skilled in the art for this type of reaction. Suitable reactors are described for example in known reference work related to industrial chemistry such as "Ullmanns Enzyklopädie der technischen Chemie". Suitable pressure-resistant reactors are also known to a person skilled in the art and are described in known reference work related to industrial chemistry such as "Ullmanns Enzyklopädie der technischen Chemie". Preferably, for the hydrogenation in reaction step i) an autoclave is employed which may have an internal stirrer and an internal lining.

The hydrogenation in reaction step i) is generally performed at the partial pressure of hydrogen at the respective reaction temperature. Preferably, the hydrogen pressure is in the range from 1 to 700 bar, more preferably from 1 to 600 bar and even more preferably from 1 to 300 bar. The hydrogen pressure can be adjusted depending on the activity of the employed hydrogenation catalyst.

Preferably, after the hydrogenation in reaction step i) the compound of the formula (V), preferably 1,6-hexanediol, is separated at least partially from the reaction mixture comprising the compound of the formula (V), non-converted compounds of the formula (I), non-converted alkanols of the formula (III), optionally the solvent and optionally water. The separation of the compound of the formula (V) can principally be performed by all separation methods known to a person skilled in the art. Preferably, the compound of the formula (V) is separated by distillation, crystallization, extraction, adsorption or a combination of these methods. Particularly preferably, the compound of the formula (V) is separated by distillation. The distillation can be performed by methods which are principally known to a person skilled in the art. Preferably, the distillation is performed in a vaporizer or in a distillation unit comprising a vaporizer and one or more distillation columns with trays or a packing.

Preferably, the reaction mixture obtained in the hydrogenation of reaction step i) is subjected to at least one separation step in order to separate partially at least one of the following components:
the at least one transition metal catalyst TMC 3,
the non-converted at least one alkanol of the formula (III),
the non-converted at least one compound of the formula (I),
reaction products different from the compounds of the formula (V),
the solvent.

These components are separated by methods principally known to a person skilled in the art. Preferably, the at least one separation step is a distillation, crystallization, extraction, adsorption or a combination of these methods.

Preferably, at least one component selected from the non-converted at least one alkanol of the formula (III), the non-converted at least one compound of the formula (I) and the at least one transition metal catalyst TMC 3 is recycled to reaction step i) of the process of the invention. The at least one transition metal catalyst can generally be employed for further hydrogenations.

The compound of the formula (V), in particular 1,6-hexanediol, is obtained in high yield, based on the compound of the formula (I), in particular butadiene.

The advantages of the two-stage hydroformylation process of the present invention are the opportunity to use higher concentrations of the compound of formula (II) in the first hydroformylation reaction in order to increase the space-time-yield and to avoid an undesired hydrogenation of the remaining C—C double bond. In the second hydroformylation reaction the n/i selectivity is increased by running the formylation reaction in the presence of an organic base and an appropriate transition metal catalysts TMC 2. The improvements in both hydroformylation steps result in a better overall yield of the compounds of the formula (IV) based on the compounds of the formula (II).

Another aspect of the present invention provides a process for producing a compound of the formula (V)

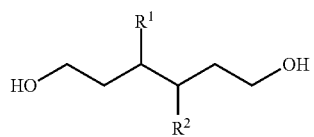

wherein
$R^1$ and $R^2$ are independently from each other hydrogen or linear or branched $C_1$-$C_4$-alkyl,
Z is a hydrocarbon chain having 2 or 3 carbon atoms which is unsubstituted or substituted and which may be part of a carbocycle, a heterocycle or an aromatic or heteroaromatic ring,
comprising the process step
i) reacting a compound of the formula (I)

(I)

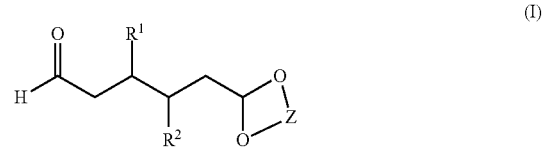

wherein
$R^1$ and $R^2$ have the same meaning as in formula (V) and
Z is a hydrocarbon chain having 2 or 3 carbon atoms which is unsubstituted or substituted and which may be part of a carbocycle, a heterocycle or an aromatic or heteroaromatic ring,
with hydrogen in the presence of at least one transition metal catalyst TMC 3 and in the presence of water, preferably wherein the molar ratio of water to the compound of formula (I) is at least 1,
wherein during the hydrogenation the temperature is increased for at least 20 K from a temperature $T_1$ to a temperature $T_2$.

The description and preferred embodiments of the compound of the formula (I), the transition metal catalyst TMC 3 and the particular conditions of the hydrogenation step, such as the applied hydrogen pressure, the temperatures $T_1$ and $T_2$, the reaction time or the amount of water in the reaction mixture corresponds to the above description of these features for reaction step i) of the above-described process of the invention comprising the two-stage hydroformylation process. In the present inventive hydrogenation process the origin of compound of the formula (I) is no limited to the above-described two-stage hydroformylation process.

The hydrogenation of compounds of formula (I) to compounds of formula (V), wherein during the hydrogenation the temperature is increased for at least 20 K from a temperature $T_1$ to a temperature $T_2$, results in a higher selectivity related to the compounds of formula (V) compared with processes, wherein the temperature is kept constant.

The invention is illustrated by the examples which follow, but these do not restrict the invention.

Figures in percent are each based on % by weight, unless explicitly stated otherwise.

I. Synthesis of 1,6-hexanediol

I.1 Preparation of Butenyl Acetals Via Mono-Hydroformylation of Butadiene

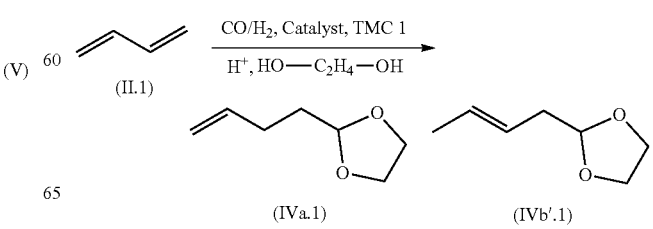

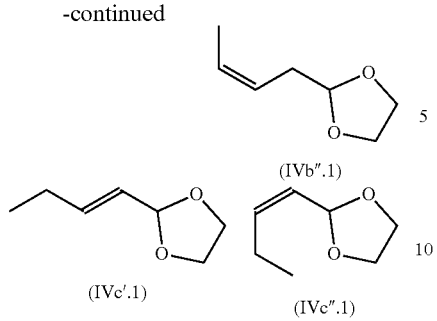

(IVc'.1) (IVb".1) (IVc".1)

I.1.a General Procedure for Catalyst Formation

Catalyst precursor 0.1002 g Rh(CO)$_2$[acac] and Ligand 1.0035 g L4 were separately dissolved in 36 g toluene and under nitrogen atmosphere quantitatively transferred in Glovebox into autoclave. Autoclave was directly closed, pressurized with nitrogen. Autoclave was fitted in bath and purged with nitrogen. Experiment was carried out in autoclave chamber and catalyst was preformed with synthesis gas 10 bar CO/H$_2$=1:1 at elevated temperature 70° C. for 30 minutes.

I.1.b General Procedure for Butadiene Hydroformylation to Butenylacetals

After catalyst preformation 60 g ethylene glycol with 0.009 g trifluoroacetic acid were added via HPLC pump. After completion 24 g 1,3-butadiene was dosed with help of scale indicator and the reaction parameters were adjusted to 30 bar CO/H$_2$=1:1 and 60° C. After 8 hours was the autoclave cooled to 40° C. and for 15 minutes at a slower stirring rate outgassed. Autoclave was flushed with nitrogen and opened. Both phases were separated from one another, upper pale yellow product phase 41.9 g and the down layered colorless ethylene glycol phase 74 g. The GC analysis of upper phase showed residual 1,3-butadiene 43.8%, hydrogenation product 2-butyl-1,3-dioxolane 1% and products 2-but-3-enyl-1,3-dioxolane 5.7%, 2-[(E)-but-2-enyl]-1,3-dioxolane 31.6%, 2-[(Z)-but-2-enyl]-1,3-dioxolane 9.9%, 2-[2-(1,3-dioxolan-2-yl)butyl]-1,3-dioxolane/2-[3-(1,3-dioxolan-2-yl)butyl]-1,3-dioxolane 1.2%, 2-[4-(1,3-dioxolan-2-yl)butyl]-1,3-dioxolane 4.6% (toluene not included).

All 14 Experiments were combined and crude product distilled under 0.1 mbar pressure over tower packing column filled with 3 mm glass beads. The first fraction 1.9 g was collected up to 40° C. transition temperature with an 80.9% product purity, the second fraction 3.0 g at 40-45° C. with a 92.7% product purity, the third fraction 15.6 g at 45-60° C. 98.2% product purity, fourth fraction 26.4 g at 60-70° C. with an 98.9% purity, fifth fraction 12.1 g at 70-80° C. with an 99.1% product purity and cold trap with 405 g solvents.

I.2 Preparation of n-Pentanal-Acetal Via Hydroformylation of Butenyl Acetals

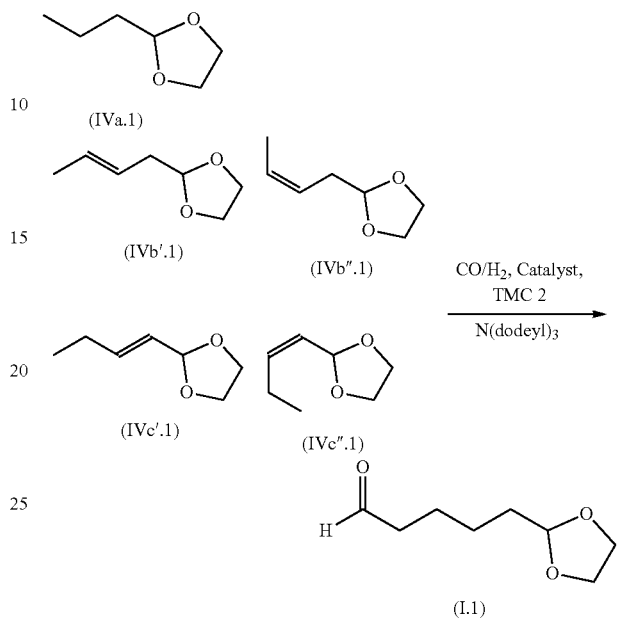

I.2.a General Procedure for Catalyst Formation

Catalyst precursor 0.0255 g Rh(CO)$_2$[acac] and Ligand 0.415 g L4 were separately dissolved in 10 g toluene and with syringe transferred into autoclave previously flushed with CO/H$_2$=1:1. At 5 bar pressure and 100° C. was active catalyst formed.

I.2.b General Procedure for Hydroformylation of Butenyl Acetals

After catalyst preformation 15.0 g Butenylacetal and 0.53 g Tridodecylamine were added via syringe. Autoclave was pressurized with 5 bar CO/H$_2$=1:1 and the reaction mixture stirred at 100° C. After 4 hours 70.8% Butenylacetal was converted to 10.4% iso-Pentanalacetale, 56.4% n-Pentanal-acetal and 4% hydrogenation products. The N-content of hydroformylation product was 84.4%.

The crude product was distilled with 10 g Tridodecylamine at 1 mbar pressure. The first fraction 9.7 g up to 30° C. transition temperature with 99.1% product purity and the second fraction 12.3 g at 69-72° C. with 98.0% product purity.

Results summarized in Table 1

|  | Exp. 1. | Exp. 2 | Exp. 3 | Exp. 4 | Exp. 5 | Exp. 6 | Exp. 7 |
|---|---|---|---|---|---|---|---|
| Butenylacetal (g) | 15.0 | 2.0 | 2.0 | 2.0 | 2.0 | 2.0 | 2.0 |
| Rh(CO)$_2$[acac] (g) | 0.0255 | 0.0255 | 0.0255 | 0.0255 | 0.0051 | 0.0051 | 0.0051 |
| Ligand (g) | 0.415 (L4) | 0.415 (L4) | 0.474 (UCC2) | 0.474 (UCC2) | 0.084 (MeSkatOx) | 0.0947 (UCC2) | 0.083 (L4) |
| Toluene (g) | 10.0 | 18.0 | 18.0 | 18.0 | 18.0 | 18.0 | 18.0 |
| Tridodecylamine (g) | 0.53 | 0.53 | 0.53 | — | — | — | — |
| Rhodium (ppm) | 392 | 485 | 484 | 497 | 101 | 101 | 101 |
| Rh:Ligand | 1:5 | 1:5 | 1:5 | 1:5 | 1:5 | 1:5 | 1:5 |
| Ligand:Amine | 1:0.5 | 1:0.5 | 1:0.5 | — | — | — | — |

|  | Exp. 1. | Exp. 2 | Exp. 3 | Exp. 4 | Exp. 5 | Exp. 6 | Exp. 7 |
|---|---|---|---|---|---|---|---|
| Preformation | 5 bar CO/H$_2$ (1:1) 0.5 h, 100° C. | 5 bar CO/H$_2$ (1:1) 0.5 h, 100° C. | 5 bar CO/H$_2$ (1:1) 0.5 h, 100° C. | 5 bar CO/H$_2$ (1:1) 0.5 h, 80° C. | 5 bar CO/H$_2$ (1:1) 0.5 h, 75° C. | 5 bar CO/H$_2$ (1:1) 0.5 h, 75° C. | 5 bar CO/H$_2$ (1:1) 0.5 h, 65° C. |
| Reaction | 5 bar CO/H$_2$ (1:1) 4 h, 100° C. | 5 bar CO/H$_2$ (1:1) 2 h, 100° C. | 5 bar CO/H$_2$ (1:1) 2 h, 100° C. | 5 bar CO/H$_2$ (1:1) 10 h, 80° C. | 5 bar CO/H$_2$ (1:1) 10 h, 75° C. | 5 bar CO/H$_2$ (1:1) 10 h, 75° C. | 5 bar CO/H$_2$ (1:1) 0.5 h, 65° C. |
| Conversion (%) | 70.8 | 99.8 | 68.6 | 68.6 | 25.4 | 17.7 | 5.3 |
| N-content (%) | 84.4 | 93.0 | 90.7 | 79.2 | 59.6 | 86.3 | 82.7 |
| Hydrogenation (%) | 4.0 | 7.1 | 0 | 22.5 | 0 | 0 | 0 |
| Iso-Pentanal-acetale (%) | 10.4 | 6.5 | 6.4 | 3.8 | 10.3 | 2.4 | 0.9 |
| n-Pentanal-acetal (%) | 56.4 | 86.2 | 62.3 | 14.4 | 15.2 | 15.2 | 4.4 |
| Diacetale (iso/n) | 0 | 0 | 0 | 4.1/23.9 | 0 | 0 | 0 |

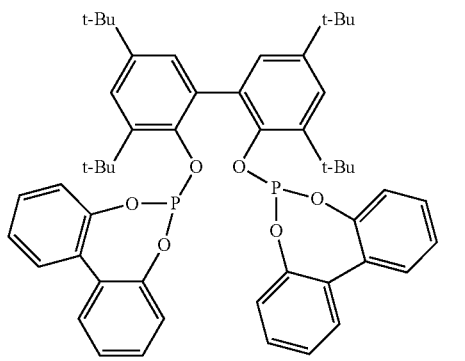

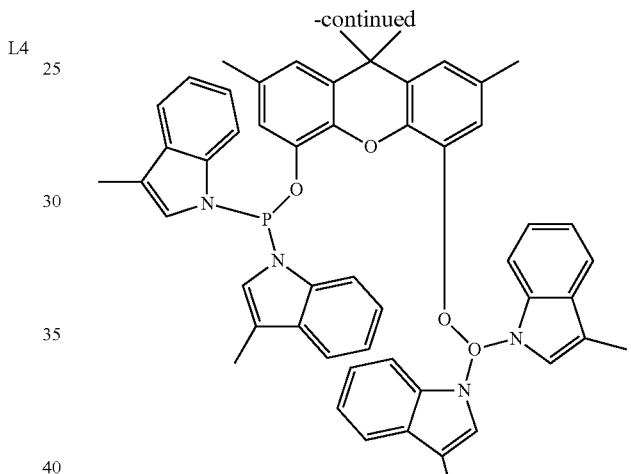

MeSkatOx

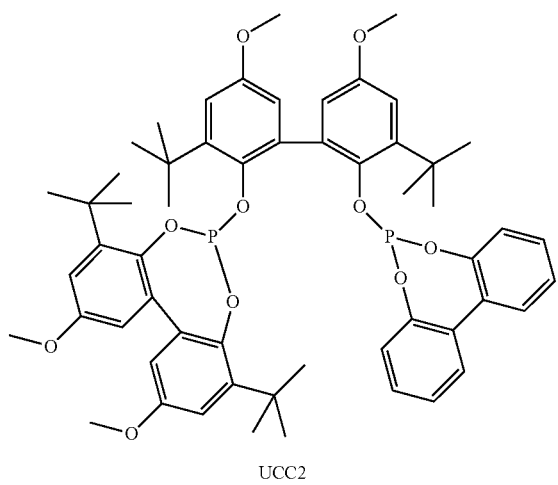

UCC2

I.3 Preparation of 1,6-Hexanediol by Hydrogenation of n Pentanal-Acetal

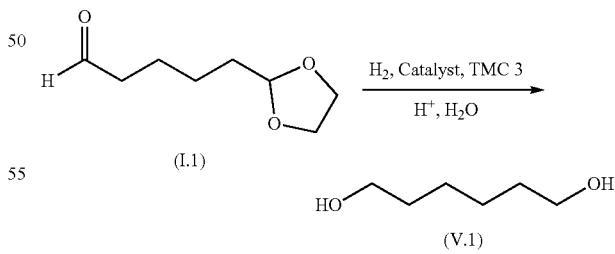

An autoclave is filled using the following procedure and then closed.

a) Catalyst (NiO@SiO$_2$, 2,5%) filled in the autoclave as a fine powder in dry form.
b) Autoclave purged twice with 0.5 bar N$_2$.
c) Starting material (1 equiv) and water (1.5 equiv) added in the autoclave.

The autoclave is then closed, purged twice with 2 bar $N_2$, purged three times with 20 bar $H_2$ and then cold filled with 20 bar $H_2$.

The system is then warmed up to 80° C. and stirred; pressure rises to 40 bar.

After 2 h reacting at 80° C., the temperature is brought to 180° C. and the mixture let to react for another 2 h. The autoclave is then let cool down to RT and the reaction mixture filtered (0.45μ Teflon filter) to separate the catalyst from the product (95% 1,6-hexanediol).

The invention claimed is:

1. A two-stage hydroformylation process for producing a compound of the formula (I)

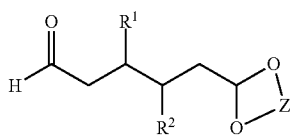
(I)

wherein
R$^1$ and R$^2$ are independently from each other hydrogen or linear or branched $C_1$-$C_4$-alkyl,
Z is a hydrocarbon chain having 2 or 3 carbon atoms which is unsubstituted or substituted and which may be part of a carbocycle, a heterocycle or an aromatic or heteroaromatic ring,
comprising the process steps:
a) reacting at least one compound of the formula (II)

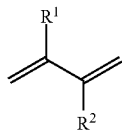
(II)

wherein R$^1$ and R$^2$ have the same meaning as in formula (I),
with carbon monoxide and hydrogen in the presence of at least one transition metal catalyst TMC 1,
wherein the reaction is performed in the presence of at least one alkanol of the formula (III)

HO—Z—OH  (III)

wherein Z has the same meaning as in formula (I),
and in the presence of at least one acid,
to obtain a reaction mixture comprising at least one compound selected from the compounds of the formulas (IVa), (IVb'), (IVb"), (IVc') and (IVc"),

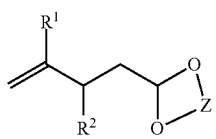
(IVa)

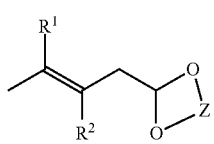
(IVb')

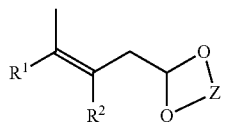
(IVb")

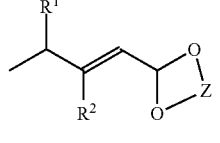
(IVc')

(IVc")

wherein R$^1$, R$^2$ and Z have the same meaning as in formula (I), b) separating the reaction mixture formed in process step a) to obtain a fraction enriched with at least one compound selected from the compounds of the formulas (IVa), (IVb'), (IVb"), (IVc') and (IVc") and depleted from the alkanol of the formula (III) and from the transition metal catalyst TMC 1, c) reacting the fraction enriched with at least one compound selected from the compounds of the formulas (IVa), (IVb'), (IVb"), (IVc') and (IVc") obtained in process step b) with carbon monoxide and hydrogen in the presence of at least one transition metal catalyst TMC 2 and at least one organic base to obtain the compound of the formula (I), wherein the organic base is used in a molar amount, which is equivalent or higher than the molar amount of the acid, which was used in process step a), and which is present in the fraction obtained in process step b), and d) optionally separation of the reaction mixture formed in process step c) to obtain a fraction enriched with the compound of the formula (I) and wherein the at least one transition metal catalyst TMC 1 used in process step a) and the at least one transition metal catalyst TMC 2 used in process step c) both comprise Rh.

2. A process for producing a compound of the formula (V)

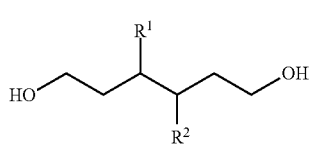
(V)

wherein
R$^1$ and R$^2$ are independently from each other hydrogen or linear or branched $C_1$-$C_4$-alkyl, comprising the process steps a), b), c) and d) for producing the compound of the formula (I) according to claim 1,

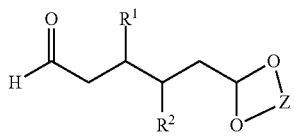

(I)

wherein $R^1$ and $R^2$ have the same meaning as in formula (V) and

Z is a hydrocarbon chain having 2 or 3 carbon atoms which is unsubstituted or substituted and which may be part of a carbocycle, a heterocycle or an aromatic or hero-aromatic ring, followed by a process step:

i) reacting the compound of formula (I) with hydrogen in the presence of at least one transition metal catalyst TMC 3 and in the presence of water, wherein during the hydrogenation in process step i) the temperature is increased for at least 20 K from a temperature $T_1$ to a temperature $T_2$.

3. The process according to claim 1, wherein the at least one compound of the formula (II) is butadiene.

4. The process according to claim 1, wherein the molar ratio of the at least one compound of the formula (II) to the at least one alkanol of the formula (III) is in the range from 1:1 to 1:100.

5. The process according to claim 1, wherein the acid used in process step a) has a $pK_a$-value relative to water in the range from −14 to 7.

6. The process according to claim 2, wherein the acid used in process step a) has a $pK_a$-value relative to water in the range from −2 to 5.

7. The process according to claim 1, wherein the at least one transition metal catalyst TMC 1 used in process step a) and the at least one transition metal catalyst TMC 2 used in process step c) each comprise independently from each other at least one bidentate ligand which is bound over two P atoms to a transition metal.

8. The process according to claim 1, wherein the at least one transition metal catalyst TMC 1 used in process step a) and the at least one transition metal catalyst TMC 2 used in process step c) both comprise at least one bidentate ligand selected from the compounds of the formula (VI.a), (VI.b), (VI.c), (VI.d) and (VI.e),

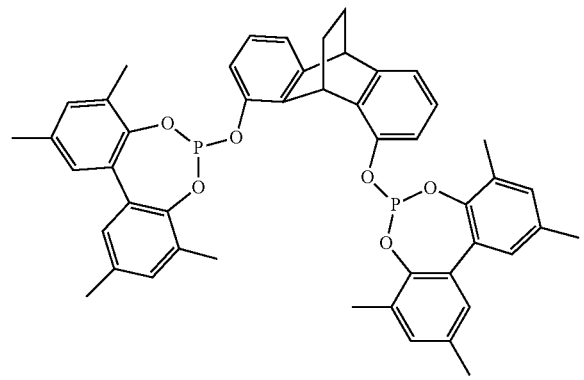

(VI.a)

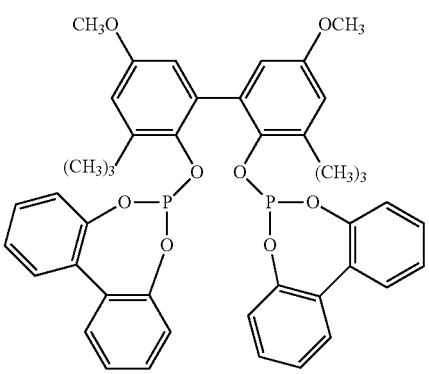

(VI.b)

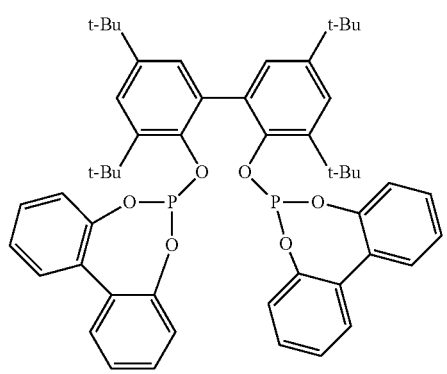

(VI.c)

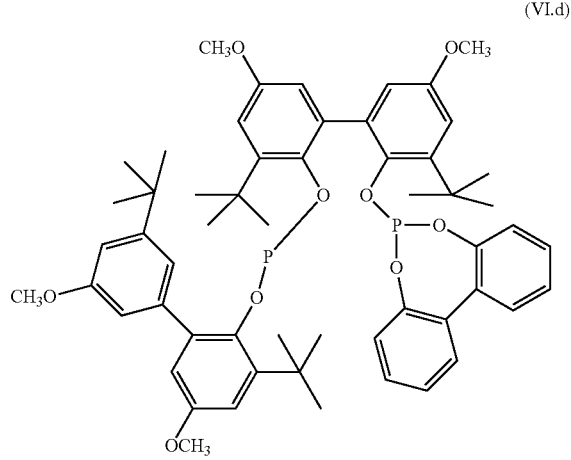

(VI.d)

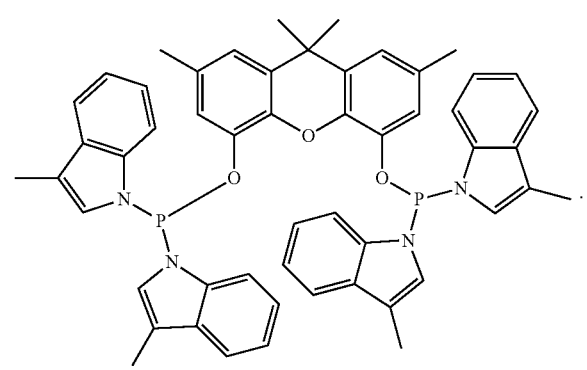

(VI.e)

9. The process according to claim 1, wherein the organic base used in process step c) is an amine of formula (VII)

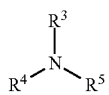

(VII)

wherein
R³ is hydrogen or an organic radical selected from linear or branched, substituted or unsubstituted $C_1$-$C_{30}$-alkyl,
R⁴ and R⁵ are independently from each other hydrogen or an organic radical selected from linear or branched, substituted or unsubstituted $C_1$-$C_{30}$-alkyl,
or two adjacent radicals of the group of radicals consisting of R³, R⁴ and R⁵ together with the atoms connecting them form a monocyclic or polycyclic, substituted or unsubstituted, aliphatic ring system which has from 4 to 40 carbon atoms and can also comprise heteroatoms selected from the group consisting of the elements N, P, O and S.

10. The process according to claim 2, wherein in process step i) $T_1$ is in the range from 40 to 120° C. and $T_2$ is in the range from 140 to 220° C.

11. The process according to claim 2, wherein the at least one transition metal catalyst TMC 3 used in process step i) comprises at least one transition metal selected from Ru, Ir, Rh, Ni, Pd and Pt.

\* \* \* \* \*